US006069121A

United States Patent [19]

Cassady et al.

[11] Patent Number: 6,069,121

[45] Date of Patent: May 30, 2000

[54] SUPERFATTED PERSONAL CLEANSING BAR CONTAINING ALKYL POLYGLYCOSIDE

[75] Inventors: Timothy J. Cassady, Hamilton; Robert R. Schoettker, Cincinnati, both of Ohio

[73] Assignee: Henkel Corporation, Gulph Mills, Pa.

[21] Appl. No.: 09/292,410

[22] Filed: Apr. 15, 1999

Related U.S. Application Data

[60] Provisional application No. 60/085,683, May 15, 1998.

[51] Int. Cl.[7] .............................. A61K 7/50; C11D 17/00

[52] U.S. Cl. .......................... 510/151; 510/152; 510/155; 510/470; 510/481; 510/491

[58] Field of Search .................................... 510/151, 152, 510/155, 470, 481, 488, 491

[56] References Cited

U.S. PATENT DOCUMENTS

| | | | |
|---|---|---|---|
| 1,985,424 | 12/1934 | Piggott | 260/124 |
| 2,965,576 | 12/1960 | Wilson | 252/137 |
| 4,820,438 | 4/1989 | Zilch | 252/108 |
| 5,194,639 | 3/1993 | Connor et al. | 554/66 |
| 5,266,690 | 11/1993 | McCurry, Jr. et al. | 536/18.6 |
| 5,312,559 | 5/1994 | Kacher et al. | 252/125 |
| 5,334,764 | 8/1994 | Scheibel et al. | 564/487 |
| 5,631,215 | 5/1997 | Kinsman | 510/130 |
| 5,705,462 | 1/1998 | Hormes et al. | 510/141 |
| 5,712,235 | 1/1998 | Nieendick et al. | 510/151 |

*Primary Examiner*—Necholus Ogden
*Attorney, Agent, or Firm*—John E. Drach; Steven J. Trzaska

[57] ABSTRACT

A process for making a superfatted personal cleansing bar involving the steps of: (a) providing a solid-form superfatting agent consisting of: (i) a fatty component selected from the group consisting of $C_6$–$C_{22}$ free fatty acids, $C_6$–$C_{22}$ fatty alcohols, and mixtures thereof; and (ii) a nonionic sugar surfactant selected from the group consisting of an alkyl polyglycoside of formula I:

$$R_1O(Z)_a \qquad I$$

wherein $R_1$ is a monovalent organic radical having from about 6 to about 30 carbon atoms; Z is a saccharide residue having 5 or 6 carbon atoms; and a is a number having a value from 1 to about 6, a polyhydroxy fatty acid amide, and mixtures thereof; (b) providing a solid-form neutralized tallow/coco fatty acid soap mixture; (c) mixing components (a) and (b) to form a superfatted soap bar stock; and (d) stamping the superfatted soap bar stock into a finished personal cleansing bar.

30 Claims, No Drawings

SUPERFATTED PERSONAL CLEANSING BAR CONTAINING ALKYL POLYGLYCOSIDE

CROSS-REFERENCE TO RELATED APPLICATIONS

This application claims the benefit of copending provisional application Ser. No. 60/085,683, filed on May 15, 1998.

STATEMENT REGARDING FEDERALLY SPONSORED RESEARCH OR DEVELOPMENT

Not Applicable.

BACKGROUND OF THE INVENTION

This invention relates to a process for making superfatted soap bars. Soap in bar form has long been in use for cleansing purposes. Those skilled in the art use the term soap to designate the reaction product of a carboxylic acid with a base, typically a metal hydroxide or carbonate. The resulting salt has both a polar hydrophilic end and a non-polar lipophilic end which facilitates the removal of oils and other non-polar materials from the skin or other surface in the presence of water.

Bar soaps are customarily prepared either by framing/casting or by refining/plodding. Framed or cast soaps are prepared by reacting an appropriate fat, oil or carboxylic acid with a base in the presence of water to form soap, pouring the molten soap containing about 30% water into a frame or a mold, allowing the soap to cool and harden, and removing the soap having about 20% to 25% water by weight in a bar form. Those skilled in the soap-making art are aware that the carboxylic acid hereafter referred to as a fatty acid is readily available as an article of commerce. The fatty acid also can be obtained from a fat, such as tallow or lard, from an oil, such as coconut oil, palm oil, palm kernel oil, or olive oil, or from combinations of fats and oils. Fats and oils are comprised in substantial part of glycerides of varying chain lengths, which are esters of glycerol (glycerine) and fatty acids. Under alkaline conditions, and in the presence of heat, the glycerides constituting the fats and oils break down to form fatty acid salts, also known as soaps, and glycerine.

Refined/plodded soap bars are produced by subjecting the neutralized soap to various finishing steps which alter the crystalline matrix of the soap from the omega phase, as formed in framed/cast soap bars, to the beta phase. Prior to conversion the soap is first dried from a moisture level of approximately 30% to a level in the range of about 10% to about 14%. Next, the dried soap is generally sent to a simple paddle-type mixer where a variety of additives can be introduced. From this mixer the soap is then sent either directly to a refiner or optionally to a three-roll mill and then to the refiner. Both the refiner and the mill subject the soap to compression and an intense shearing action which tend to orient the soap crystals and convert the soap largely to the beta-phase. After refining, the soap is compressed into a dense, coherent form in a plodding operation which forms solid portions which are suitable for stamping into bars.

The drying step is necessary to remove the "gummy" texture and excessive pliability of the soap mass which exist typically at higher moisture levels. In the production of plodded bars, drying to from about 10% to about 147% moisture is necessary to permit the soap mass to be processed through the finishing equipment. Drying on a commercial basis is achieved by several different methods. One procedure employs a water-chilled roll in combination with a second feed roll to spread molten, neutralized soap into a thin, uniform layer. The cooled soap is then scraped from the roll to form chips and dried to a specific moisture level in a tunnel dryer. Soap chips already having a low moisture level (about 10% to 11%) are further dried by repeatedly conducting the chips through close-set water cooled steel rolls (i.e., three-roll mill) in the procedure known as milling described above. A relatively modern technique for the drying of soap is known as spray drying. This process directs molten soap to the top of a tower via spray nozzles. The sprayed soap hardens and then dries in the presence of a current of heated air. Vacuum may be applied to facilitate the removal of water. Though typically the moisture level of plodded soap bars is maintained in the range of about 10% to about 14%, a plodded soap bar containing greater than 14% moisture is known in the prior art.

Regular soap can have a tendency to defat the skin owing to its slightly alkaline character. This can be a problem, particularly to people with dry skin. The incorporation of a superfatting agent containing a free fatty acid into a soap bar imparts enhanced tactile properties to the composition by eliminating the effect of free alkali on the user's skin. The presence of free fatty acid also affects the bubble size of the lather formed by the soap bar by imparting a perception of a richer, creamier lather.

Prior to the present invention, however, the incorporation of free fatty acids as a solid into soap bars has not been possible. Solid forms of free fatty acids, such as stearic acid, when mixed with a solid-form soap, result in the formation of particulates or grit which cannot be completely eliminated during the refining step, which involves the passage of the material through a sequence of screens of several mesh sizes. Molten free fatty acids, which are solids at room temperature, on the other hand, crystallize when added to solid soap in the mixer also resulting in the formation of grit in the finished soap bar.

The presence of an alkyl polyglycoside in a soap produces a bar which exhibits increased flash foaming and a richer and creamier lather.

BRIEF SUMMARY OF THE INVENTION

The present invention relates to a process for making a superfatted personal cleansing bar having improved tactile and foaming properties involving the steps of:

(a) providing a solid-form superfatting agent consisting of:

(i) a fatty component selected from the group consisting of $C_6$–$C_{22}$ free fatty acids, $C_6$–$C_{22}$ fatty alcohols, and mixtures thereof; and (ii) a nonionic sugar surfactant selected from the group consisting of an alkyl polyglycoside of formula I:

$$R_1O(Z)_a \quad \text{I}$$

wherein $R_1$ is a monovalent organic radical having from about 6 to about 30 carbon atoms; Z is a saccharide residue having 5 or 6 carbon atoms; and a is a number having a value from 1 to about 6, a polyhydroxy fatty acid amide, and mixtures thereof;

(b) providing a solid-form neutralized tallow/coco fatty acid soap mixture;

(c) mixing components (a) and (b), followed by refining and plodding steps, to form a superfatted soap bar stock; and (d) stamping the superfatted soap bar stock into personal cleansing bars.

The process according to the invention produces a personal cleansing bar which is mild to the skin, lathers easily, prevents scum formation, is biodegradable and exhibits increased flash foaming and a richer, creamier lather.

BRIEF DESCRIPTION OF THE SEVERAL VIEWS OF THE DRAWING

Not Applicable.

DETAILED DESCRIPTION OF THE INVENTION

Other than in the claims and in the operating examples, or where otherwise indicated, all numbers expressing quantities of ingredients or reaction conditions used herein are to be understood as modified in all instances by the term "about".

The solid-form superfatting agent of the present invention consists of a fatty component and a nonionic sugar surfactant. The fatty component employed in the present invention is selected from the group consisting of $C_6$–$C_{22}$ free fatty acids, and preferably $C_{14}$–$C_{20}$ fatty acids, $C_6$–$C_{22}$ fatty alcohols, and preferably $C_{14}$–$C_{18}$ fatty alcohols, and mixtures thereof.

In a preferred embodiment of the present invention, the free fatty acids employed are stearic-palmitic acid combinations commercially available as "stearic acid" or "palmitic acid" and which are predominantly comprised of stearic acid and palmitic acid. In a particularly preferred embodiment, the fatty acid component contains from 45% to 65% by weight stearic acid and from 25% to 55% by weight of palmitic acid.

The fatty alcohols which may be employed as the fatty component are the saturated and unsaturated $C_8$ to $C_{20}$ alcohols. Examples of saturated fatty alcohols which may be used include, but are not limited to, octyl, decyl, lauryl, myristyl, cetyl and stearyl alcohols. Suitable unsaturated fatty alcohols include, for example, oleyl, linoleyl and linolenyl alcohols.

The nonionic sugar surfactants which may be employed to formulate the superfatting agent include alkyl polyglycosides, polyhydroxy fatty acid amides, and mixtures thereof. The alkyl polyglycosides which can be used in the compositions according to the invention are represented by formula I $$R_1O(R_2O)_b(Z)_a \qquad \text{I}$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6. Preferred alkyl polyglycosides which can be used in the compositions according to the invention have the formula I wherein Z is a glucose residue and b is zero. Such alkyl polyglycosides are commercially available, for example, as APG®, GLUCOPON®, or PLANTAREN® surfactants from Henkel Corporation, Ambler, Pa., 19002. Examples of such surfactants include but are not limited to:

1. APG® 225 Surfactant—an alkyl polyglycoside in which the alkyl group contains 8 to 10 carbon atoms and having an average degree of polymerization of 1.7.
2. GLUCOPON® 425 Surfactant—an alkyl polyglycoside in which the alkyl group contains 8 to 16 carbon atoms and having an average degree of polymerization of 1.48.
3. GLUCOPON® 625 Surfactant—an alkyl polyglycoside in which the alkyl group contains 12 to 16 carbon atoms and having an average degree of polymerization of 1.6.
4. APG® 325 Surfactant—an alkyl polyglycoside in which the alkyl group contains 9 to 11 carbon atoms and having an average degree of polymerization of 1.5.
5. GLUCOPON® 600 Surfactant—an alkyl polyglycoside in which the alkyl group contains 12 to 16 carbon atoms and having an average degree of polymerization of 1.4.
6. PLANTAREN® 2000 Surfactant—a $C_{8-16}$ alkyl polyglycoside in which the alkyl group contains 8 to 16 carbon atoms and having an average degree of polymerization of 1.4.
7. PLANTAREN® 1300 Surfactant—a $C_{12-16}$ alkyl polyglycoside in which the alkyl group contains 12 to 16 carbon atoms and having an average degree of polymerization of 1.6.

Other examples include alkyl polyglycoside surfactant compositions which are comprised of mixtures of compounds of formula I wherein Z represents a moiety derived from a reducing saccharide containing 5 or 6 carbon atoms; a is a number having a value from 1 to about 6; b is zero; and $R_1$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and polyglycosides, in the resulting product changes and the concentration in the product of the polyglycosides relative to the monoglycoside increases as well as the concentration of individual polyglycosides to the total, i.e., DP2 and DP3 fractions in relation to the sum of all DP fractions. Such compositions are disclosed in U.S. Pat. No. 5,266,690, the entire contents of which are incorporated herein by reference.

Other alkyl polyglycosides which can be used in the compositions according to the invention are those in which the alkyl moiety contains from 6 to 18 carbon atoms in which the average carbon chain length of the composition is from about 9 to about 14 comprising a mixture of two or more of at least binary components of alkylpolyglycosides, wherein each binary component is present in the mixture in relation to its average carbon chain length in an amount effective to provide the surfactant composition with the average carbon chain length of about 9 to about 14 and wherein at least one, or both binary components, comprise a Flory distribution of polyglycosides derived from an acid-catalyzed reaction of an alcohol containing 6–20 carbon atoms and a suitable saccharide from which excess alcohol has been separated.

The polyhydroxy fatty acid amides which can be used to formulate the superfatting agent are represented by formula

II:

(II)

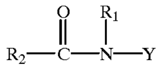

wherein: $R_1$ is H, $C_1$–$C_4$ hydrocarbyl, 2-hydroxy ethyl, 2-hydroxy propyl, or a mixture thereof, preferably $C_1$–$C_4$ alkyl, more preferably $C_1$ or $C_2$ alkyl, most preferably $C_1$ alkyl (i.e., methyl); and $R_2$ is a $C_5$–$C_3$, hydrocarbyl moiety, preferably straight chain $C_7$–$C_{19}$, alkyl or alkenyl, more preferably straight chain $C_9$–$C_{17}$ alkyl or alkenyl, most preferably straight chain $C_{11}$–$C_{19}$ alkyl or alkenyl, or mixture thereof; and Y is a polyhydroxyhydrocarbyl moiety having a linear hydrocarbyl chain with at least 3 hydroxyls directly connected to the chain, or an alkoxylated derivative (preferably ethoxylated or propoxylated) thereof. Y preferably will be derived from a reducing sugar in a reductive amination reaction; more preferably Y is a glycityl moiety. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Y. It should be understood that it is by no means intended to exclude other suitable raw materials. Y preferably will be selected from the group consisting of $—CH_2—(CHOH)_n—CH_2OH$, $—CH(CH_2OH)—(CHOH)_{n-1}—CH_2OH$, $—CH_2—(CHOH)_2(CHOR')(CHOH)—CH_2OH$, where n is an integer from 3 to 5, inclusive, and R' is H or a cyclic mono- or poly-saccharide, and alkoxylated derivatives thereof. Most preferred are glycityls wherein n is 4, particularly $—CH_2—(CHOH)_4—CH_2OH$. Compounds of the formula I are also known as glucamides. Therefore, when, for example, $R_1$ is methyl, $R_2$ is dodecyl; and Y is $—CH_2—(CHOH)_4—CH_2OH$, the compound in question is referred to as dodecyl N-methylglucamide.

Methods for making polyhydroxy fatty acid amides are known in the art. In general, polyhydroxy fatty acid amides can be made by reductively aminating a reducing sugar reacting with an alkyl amine to form a corresponding N-alkyl polyhydroxyamine and then reacting the N-alkyl polyhydroxyamine with a fatty aliphatic ester or triglyceride to form the N-alkyl, polyhydroxy fatty acid amide. Processes for making polyhydroxy fatty acid amides are disclosed in U.S. Pat. Nos., 1,985,424; 2,965,576; 5,194,639; and 5,334,764, the entire contents of each of which is incorporated herein by reference.

In a particularly preferred embodiment of the present invention, the nonionic sugar surfactant is an alkyl polyglycoside of formula I wherein $R_1$ is an alkyl group having from 10 to 14 carbon atoms, b is zero, and a is a number having a value of about 1.4.

The preparation of the superfatting agent of the invention involves heating both the fatty component, preferably stearic acid, and the nonionic sugar surfactant, preferably an alkyl polyglycoside, to a temperature of about 80° C. The heated fatty component and nonionic sugar surfactant are then combined, with stirring, transferred to the heated reservoir of a chilled roll flaking unit and flaked, thereby forming a solid superfatting agent. The solid superfatting agent preferably has a moisture content of up to about 15% by weight, and most preferably from about 10 to about 15% by weight, based on the weight of the superfatting agent.

In one embodiment of the present invention, the ratio by weight of fatty component:nonionic sugar surfactant is from about 1:2 to about 2:1, and preferably about 1:1. The resulting solid superfatting agent will typically contain from about 1 to about 40% by weight, and most preferably about 25% by weight of nonionic sugar surfactant, from about 1 to about 40% by weight, and most preferably about 50% by weight of fatty component, and remainder, to 100%, water, all weights being based on the weight of the solid superfatting agent.

With respect to the soap portion of the invention, it generally contains a blend of about 80% by weight tallow fatty acid and about 20% by weight coco fatty acid, wherein the blend is neutralized with an aqueous solution of a base such as sodium hydroxide, potassium hydroxide, triethanolamine and mixtures thereof. The moisture content of the soap component varies in the range from about 5 to about 30% by weight, and preferably from about 10 to about 15% by weight, based on the weight of the soap component.

A typical coco fatty acid is composed primarily of from 45% to 55% by weight lauric acid, from 15% to 23% by weight of myristic acid, from 8% to 11% of palmitic acid, from 1% to 10% by weight of stearic acid, from 1% to 14% of caprylic and capric acids, and from 1% to 8% by weight of oleic acid.

A typical tallow fatty acid is one which contains from about 45% to about 55% by weight of a mixture of saturated fatty acids a majority of which are stearic and palmitic acids and from about 45% to about 55% by weight of a mixture of unsaturated fatty acids, a large majority of which is oleic acid and which may also contain linoleic acid and linolenic acid. As desired, the linoleic and linolenic acids may also be eliminated by hydrogenation. An example of a typical commercially available unhydrogenated tallow fatty acid is EMERY® 531 Tallow Fatty Acid, a trademark product of Henkel Corporation, Emery Group, Cincinnati, Ohio. The typical specifications for EMERY® 531 Tallow Fatty Acid are: titer 36–44° C., maximum iodine value of 45–70, acid value of 200–208, color value of 19/81 (% trans. 440/550 (nm., min.). The typical composition of EMERY® 531 Tallow Fatty Acid is: 2.5% myristic acid, 0.5% pentadecanoic acid, 27% palmitic acid, 1% margaric acid, 17% stearic acid, 4% palmitoleic acid, 42% oleic acid, 5% linoleic acid, 1% linolenic acid.

After neutralization, the soap component is cooled and then dried to a lower moisture level to permit refining and plodding using soap finishing equipment well known in the art. Typically, the soap is dried to a moisture level of from about 10 to about 145% by weight.

The soap component is employed as a solid, preferably in the form of extruded noodles. The solid superfatting agent is then mixed with the solid soap noodles in a conventional mixing apparatus such as an agglomerator to form a superfatted soap stock. This method, i.e., mixing both the superfatting agent and the soap component in "solid" form allows for the incorporation of higher levels of nonionic sugar surfactant into a soap bar formulation without any attendant stickiness or tackiness problems, such as those experienced when combining these components in "liquid" form to soap noodles.

The finished product will contain from about 5 to about 25% by weight, and preferably about 10% by weight of the above-disclosed solid superfatting agent, and from about 95 to about 75% by weight, and preferably about 90% by weight of a solid soap component, all weights being based on the weight of the finished superfatted personal cleansing bar product.

In the event that the superfatting agent is used in the preferred amount of 10% by weight, the resultant bar will contain about 2.5% nonionic surfactant solids, 5.0% fatty acid solids, 9.0–13.5% moisture and 76–81% soap solids.

It will also be recognized by those skilled in the art that auxiliaries typically employed in the art of soap making such as perfumes, surfactants, and the like, can also be used in formulating the finished superfatted personal cleansing bars without departing from the spirit of the invention.

What is claimed is:

1. A process for making a superfatted personal cleansing bar comprising the steps of:

(a) providing a solid-form superfatting agent consisting of:

(i) a fatty component selected from the group consisting of $C_6$–$C_{22}$ free fatty acids, $C_6$–$C_{22}$ fatty alcohols, and mixtures thereof; and (ii) a nonionic sugar surfactant selected from the group consisting of an alkyl polyglycoside of formula I:

$$R_1O(Z)_a \qquad I$$

wherein $R_1$ is a monovalent organic radical having from about 6 to about 30 carbon atoms; Z is a saccharide residue having 5 or 6 carbon atoms; and a is a number having a value from 1 to about 6, a polyhydroxy fatty acid amide, and mixtures thereof;

(b) providing a solid-form neutralized tallow/coco fatty acid soap mixture;

(c) mixing components (a) and (b) to form a superfatted soap bar stock; and (d) stamping the superfatted soap bar stock into a finished personal cleansing bar.

2. The process of claim 1 wherein component (a)(i) is a $C_6$–$C_{22}$ free fatty acid.

3. The process of claim 2 wherein component (a)(i) is a $C_{14}$–$C_{20}$ free fatty acid.

4. The process of claim 2 wherein component (a)(i) is stearic acid.

5. The process of claim 1 wherein component (a)(i) is a $C_6$–$C_{22}$ fatty alcohol.

6. The process of claim 5 wherein component (a)(i) is a $C_{16}$–$C_{18}$ fatty alcohol.

7. The process of claim 1 wherein component (a)(ii) is an alkyl polyglycoside of formula I.

8. The process of claim 7 wherein in formula I, $R_1$ is a monovalent organic radical having from about 10 to about 14 carbon atoms, and a is a number having a value of about 1.4.

9. The process of claim 1 wherein component (a)(ii) is a polyhydroxy fatty acid amide.

10. The process of claim 9 wherein the polyhydroxy fatty acid amide is a glucamide.

11. The process of claim 1 wherein components (a)(i) and (a)(ii) are present in the solid-form superfatting agent in a ratio by weight of from about 1:2 to about 2:1, respectively.

12. The process of claim 11 wherein components (a)(i) and (a)(ii) are present in the solid-form superfatting agent in a ratio by weight of about 1:1, respectively.

13. The process of claim 1 wherein the solid-form superfatting agent has a moisture content of up to about 30% by weight, based on the weight of the superfatting agent.

14. The process of claim 13 wherein the solid-form superfatting agent has a moisture content of from about 6 to about 25% by weight, based on the weight of the superfatting agent.

15. The process of claim 1 wherein the solid-form superfatting agent contains from about 1 to about 40% by weight of component (a)(i), from about 1 to about 40% by weight of component (a)(ii), and remainder, water, all weights being based on the weight of the superfatting agent.

16. The process of claim 1 wherein the finished personal cleansing bar contains from about 5 to about 25% by weight of component (a) and from about 95 to about 75% by weight of component (b), and remainder, water, all weights being based on the weight of the finished personal cleansing bar.

17. A process for making a superfatted personal cleansing bar comprising the steps of:

(a) providing a solid-form superfatting agent consisting of:

(i) $C_6$–$C_{22}$ free fatty acids; and (ii) a nonionic sugar surfactant selected from the group consisting of an alkyl polyglycoside of formula I:

$$R_1O(Z)_a \qquad I$$

wherein $R_1$ is a monovalent organic radical having from about 6 to about 30 carbon atoms; Z is a saccharide residue having 5 or 6 carbon atoms; and a is a number having a value from 1 to about 6, a polyhydroxy fatty acid amide, and mixtures thereof;

(b) providing a solid-form neutralized tallow/coco fatty acid soap mixture;

(c) mixing components (a) and (b) followed by refining and plodding steps to form a superfatted soap bar stock; and (d) stamping the superfatted soap bar stock into a finished personal cleansing bar.

18. The process of claim 17 wherein component (a)(i) is a $C_{14}$–$C_{20}$ free fatty acid.

19. The process of claim 18 wherein component (a)(i) is stearic acid.

20. The process of claim 17 wherein component (a)(ii) is an alkyl polyglycoside of formula I.

21. The process of claim 20 wherein in formula I, $R_1$ is a monovalent organic radical having from about 10 to about 14 carbon atoms, and a is a number having a value of about 1.4.

22. The process of claim 17 wherein component (a)(ii) is a polyhydroxy fatty acid amide.

23. The process of claim 22 wherein the polyhydroxy fatty acid amide is a glucamide.

24. The process of claim 17 wherein components (a)(i) and (a)(ii) are present in the solid-form superfatting agent in a ratio by weight of from about 1:2 to about 2:1.

25. The process of claim 24 wherein components (a)(i) and (a)(ii) are present in the solid-form superfatting agent in a ratio by weight of about 1:1.

26. The process of claim 17 wherein the solid-form superfatting agent has a moisture content of up to about 15% by weight, based on the weight of the superfatting agent.

27. The process of claim 26 wherein the solid-form superfatting agent has a moisture content of from about 6 to about 12% by weight, based on the weight of the superfatting agent.

28. The process of claim 17 wherein the solid-form superfatting agent contains from about 1 to about 40% by weight of component (a)(i), from about 1 to about 40% by weight of component (a)(ii), and remainder, water, all weights being based on the weight of the superfatting agent.

29. The process of claim 17 wherein the finished personal cleansing bar contains from about 5 to about 25% by weight of component (a), from about 95 to about 75% by weight of component (b), and remainder, water, all weights being based on the weight of the finished personal cleansing bar.

30. A process for making a superfatted personal cleansing bar comprising the steps of:

(a) providing a solid-form superfatting agent having a moisture content of about 15% by weight, based on the weight of the superfatting agent, consisting of:

(i) stearic acid; and (ii) an alkyl polyglycoside of formula I:

$$R_1O(Z)_a \qquad \text{I}$$

wherein $R_1$ is a monovalent organic radical having from about 10 to about 14 carbon atoms; Z is a saccharide residue having 5 or 6 carbon atoms; and a is a number having a value of about 1.4, wherein components (a)(i) and (a)(ii) are mixed in a ratio by weight of about 1:1, respectively;

(b) providing a solid-form neutralized tallow/coco fatty acid soap mixture;

(c) mixing components (a) and (b) to form a superfatted soap bar stock; and (d) stamping the superfatted soap bar stock into a finished personal cleansing bar containing from about 5 to about 25% by weight of component (a), from about 95 to about 75% by weight of component (b) and remainder, water, all weights being based on the weight of the finished personal cleansing bar.

* * * * *